United States Patent [19]

Willis et al.

[11] 4,271,046

[45] Jun. 2, 1981

[54] NOVEL NORCAMPHANYL-SUBSTITUTED PYRANS, METHOD FOR THEIR SYNTHESIS AND USE THEREOF IN PERFUMERY

[75] Inventors: Brian J. Willis, Bergenfield, N.J.; John W. Dittrick, Flushing, N.Y.

[73] Assignee: Fritzsche Dodge & Olcott, Inc., New York, N.Y.

[21] Appl. No.: 75,222

[22] Filed: Sep. 13, 1979

Related U.S. Application Data

[62] Division of Ser. No. 950,598, Oct. 12, 1978.

[51] Int. Cl.$^3$ .............................................. A61K 7/46
[52] U.S. Cl. ............................................... 252/522 R
[58] Field of Search .................. 226/345.1; 252/522 R

[56] References Cited

U.S. PATENT DOCUMENTS 2,422,648   6/1947   Williams et al. .................. 260/345.1

OTHER PUBLICATIONS

Chem. Rev., vol. 51, Arundale et al., p. 548.

*Primary Examiner*—Alan Siegel
*Attorney, Agent, or Firm*—Kenyon & Kenyon

[57] ABSTRACT

Norcamphanyl-substituted pyrans, their preparation and their use as olfactory components of perfume formulations are disclosed.

3 Claims, 4 Drawing Figures

NOVEL NORCAMPHANYL-SUBSTITUTED PYRANS, METHOD FOR THEIR SYNTHESIS AND USE THEREOF IN PERFUMERY

This is a division of application Ser. No. 950,598 filed Oct. 12, 1978.

This invention is concerned with certain novel chemicals containing a bicyclo[2.2.1]heptane moiety and an oxacyclohexane or oxacyclohexene moiety, a method for synthesis of such chemicals, and the use of such chemicals as olfactory constituents of perfume formulations.

More specifically, the present invention is concerned with chemicals which may be represented by the structural formula:

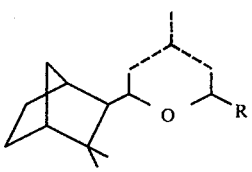

wherein the dashed lines represent either a carbon-carbon single bond or a carbon-carbon double bond, and R is either hydrogen or methyl. According to currently accepted nomenclature, and disregarding stereoisomers, the chemicals within this formula are:

When R is hydrogen:
2-(2,2-dimethylbicyclo[2.2.1]hept-3-yl)-4-methyloxacyclohex-3-ene,
2-(2,2-dimethylbicyclo[2.2.1]hept-3-yl)-4-methyloxacyclohex-4-ene, and
2-(2,2-dimethylbicyclo[2.2.1]hept-3-yl)-4-methyleneoxacyclohexane When R is methyl:
2-(2,2-dimethylbicyclo[2.2.1]hept-3-yl)-4,6-dimethyloxacyclohex-3-ene,
2-(2,2-dimethylbicyclo[2.2.1]hept-3-yl)-4,6-dimethyloxacyclohex-4-ene, and
2-(2,2-dimethylbicyclo[2.2.1]hept-3-yl)-4-methylene-6-methyloxacyclohexane The dimethylbicycloheptane moiety also may be classified as the "norcamphanyl" moiety, while the oxacyclohexane and oxacyclohexene moieties may be classified generally as "pyran" moieties. Hence, for convenience the foregoing chemicals will be referred to collectively as "norcamphanyl-substituted pyrans". The present invention is further concerned with methods for preparing the "norcamphanyl-substituted pyrans", and with their use as olfactory components of perfume compositions.

BACKGROUND OF THE INVENTION

Considerable time and effort are expended by research chemists in the search for new and inexpensive chemicals which can be used as flavor and fragrance modifiers or enhancers in various consumable materials. These substances are used to reduce or replace those natural compounds presently employed which are in diminishing or sporadic supply. They also are employed in creating entirely new flavors and fragrances.

Certain chemicals having the pyran ring have been found to be useful for imparting fragrance and/or flavor to compositions of which they are constituents. For example, Japanese application Ser. No. 7,4011-073 published Mar. 14, 1974, discloses 2,5-diethyltetrahydropyran chemicals having a rose-like scent, while 3-hydroxy-2-methyl-1,4-pyran, or maltol, is disclosed in "Perfume and Flavor Chemicals", Arctander Vol. II, No. 1831, as possessing "a warm-fruity, caramellic-sweet odor with emphasis on the caraway note in the dry state."

U.S. Pat. No. 3,901,924, granted Aug. 26, 1975, discloses certain 1,1-dialkylnaphthopyrans, as well as certain chypre and fougere type perfume formulations of which these pyrans are constituents. Examples of these pyrans are the following:

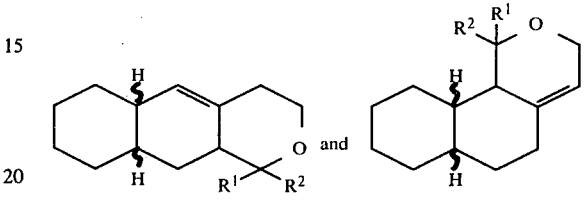

wherein each of $R^1$ and $R^2$ represents a lower alkyl group.

U.S. Pat. No. 4,010,286, granted Mar. 1, 1977, discloses various substituted spiropyrans which exhibit a variety of odors and/or flavors, including those characterized as spicy, dill, green, floral, herbal, eucalyptol-like, woody, fruity, berry-like, sweet, minty and weedy, and which are useful as flavoring and fragrance imparters or modifiers. Examples of the spiropyrans disclosed in this patent are the following:

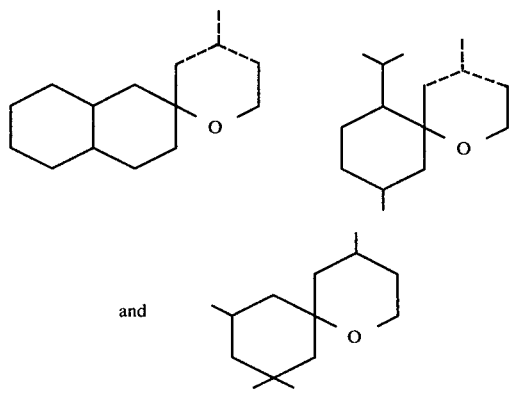

wherein the dashed lines represent carbon-carbon double bonds; and wherein the presence of two dashed lines in a single structure representation indicates a mixture of double bond isomers. Still other spiropyrans which are disclosed are the product of the reaction of dihydro verdyl ketone or verdyl ketone with 3-methyl-3-buten-1-ol, which is represented by the following formula:

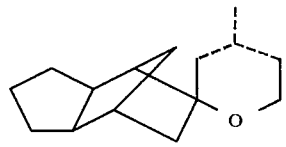

Methods of preparation of other pyran chemicals have also been disclosed in the prior art. For example, U.S. Pat. No. 2,422,648, granted June 17, 1947, discloses a method for the preparation of certain dihydropyran chemicals which comprises reacting a ketone with an unsaturated alcohol containing an unsaturated tertiary carbon atom linked directly by a single bond to a saturated carbon atom which is directly attached to the carbinol carbon atom, in the presence of an acidic condensation catalyst at a temperature of above about 50° C., but not substantially above the temperature of dehydration of the alcohol.

In addition, methods of preparation of both rose oxide and nerol oxide, known odoriferous components of Bulgarian rose oil, are disclosed in Tetrahedron Letters, 51, 4507 (1970) by J. H. P. Tyman and B. J. Willis. These chemicals are prepared from the reaction of 3-methyl-2-butenal with 2-methyl-1-buten-4-ol under acidic conditions.

The chemicals described in each of the above patents and articles are different in kind from the chemicals of the instant invention from a structural standpoint, and from the standpoint of their fragrance properties. The chemicals of the instant invention possess unexpected, unobvious and advantageous properties from the standpoint of quality, character or fragrance when used in fragrance compositions.

THE INVENTION

Figure 1:
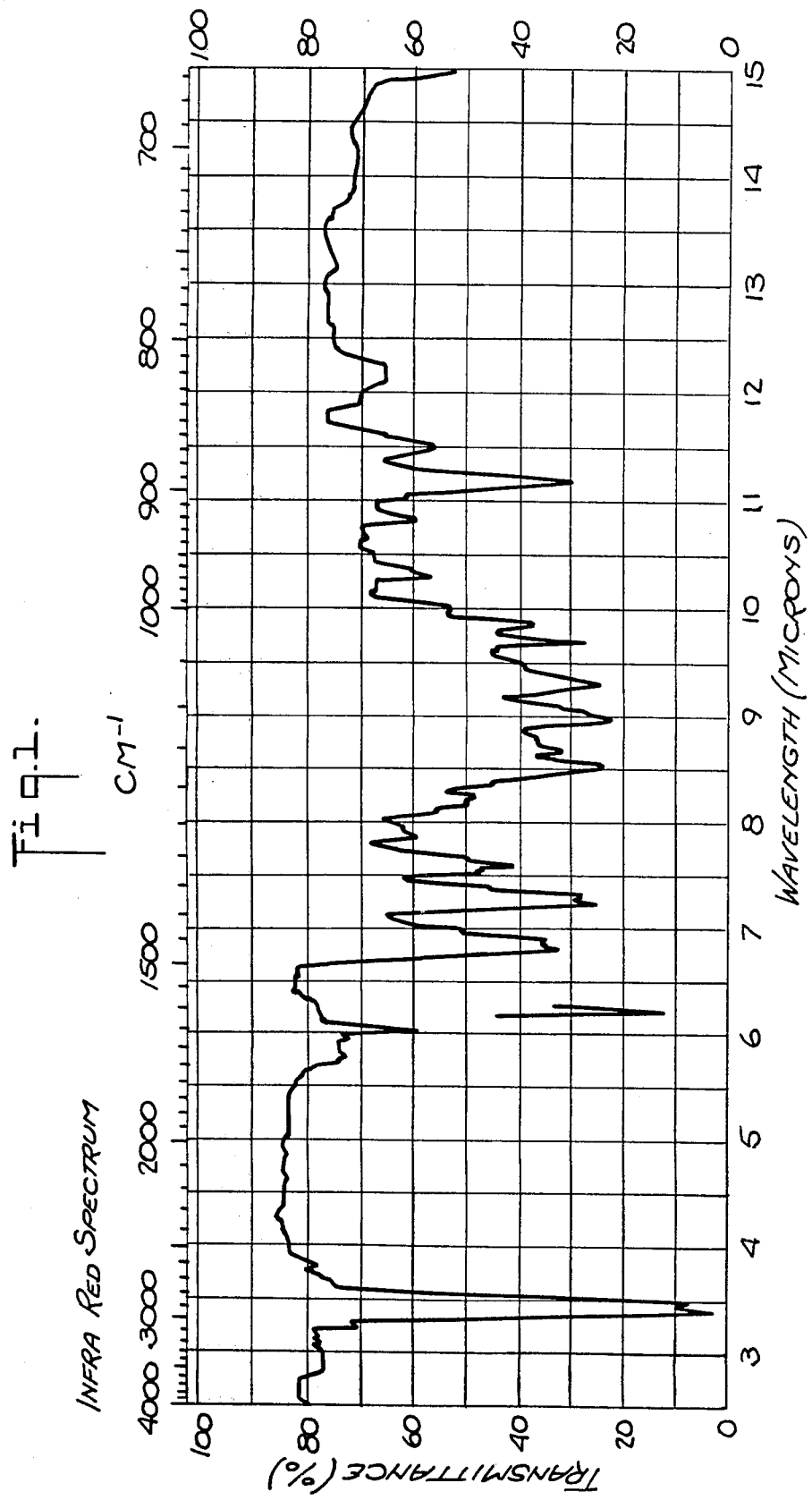
FIG. 1 represents the infra-red spectrum of the product of Example 1.

In accordance with this invention, there have been discovered novel norcamphanyl-substituted pyrans, as represented by the above formula, which are useful in perfume formulations for imparting a soft, dry woody odor with greenpepper notes to such compositions. It will be recognized that the chemicals of this invention can exist in several stereoisomeric forms, including the "dextro" and "laevo", as well as the "cis", "trans" isomers. The foregoing structural formula is intended to embrace the individual stereoisomers, as well as mixtures of the various stereoisomers of the norcamphanyl-substituted pyrans of this invention.

The novel chemicals of this invention are prepared by reacting camphene epoxide, or spiro(3,3-dimethylbicyclo[2.2.1]-heptane-2,2'-oxacyclopropane), with either 2-methyl-1-penten-4-ol or 2-methyl-1-buten-4-ol in the presence of an acid catalyst. This reaction may be represented by the general equation:

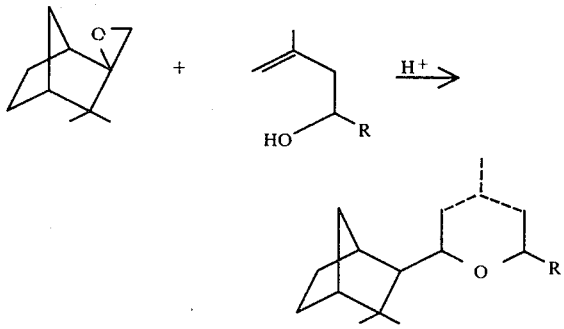

wherein R and the dashed lines have the meanings set forth above. The proportions of the two reactants is not critical, and either may be employed in molar excess. For reasons of economy, it is preferred to employ the least expensive reactant, i.e., the alkenol, in excess, for example in a molar ratio of alkenol to camphene epoxide of from about 1:1 to about 1.5:1.

Acids which may be employed as a catalyst for these reactions include inorgaic acids such as sulfuric acid and perchloric acid, and organic acids such as the sulfonic acids. Cation exchange resins, for example those containing the sulfonic acid moiety ($-SO_3H$), may be employed.

The reaction conveniently is carried out in an inert organic solvent, preferably an organic hydrocarbon solvent. Such solvents include aromatic solvents such as benzene and toluene, as well as alphatic solvents such as hexane or heptane.

Once initiated, the reaction is mildly exothermic, and it may be allowed to proceed at autogeneous temperatures, which may range from about ambient temperature up to about 60°–70° C. It is desirable, however, to heat the reaction mixture during the latter stages and to remove the water evolved during the reaction in order to maximize the yield of norcamphanyl-substituted pyrans. Temperatures of up to about 120° can be employed.

The chemicals of this invention are recovered from the reaction mixture through the use of conventional procedures, for example, the acid is neutralized and the organic products fractionated to yield a mixture of norcamphanyl-substituted pyran isomers. The mixture may be employed directly, or the isomers may be separated by techniques known to the art.

In the course of the foregoing reaction, camphene epoxide is converted in situ to the corresponding aldehyde, i.e., 2,2-dimethylbicyclo[2.2.1]heptane-3-carboxaldehyde, which then reacts with the alkenol. Consequently, the novel norcamphanyl-substituted pyrans of this invention also can be prepared by similar procedures to those described above, but substituting the aldehyde for the epoxide.

As used herein, the term "alter" is intended to mean "supply or impart an odorant character or note to an otherwise bland, relatively odorless substance, or augment or enhance the existing odor characteristics of an odorant which may be deficient in some regard, or supplement its existing odor impression to modify its quality, character or taste."

One or more of the norcamphanyl-substituted pyrans of this invention and auxiliary perfum ingredients, for example, alcohols, aldehydes, ketones, nitriles, esters, and essential oils, may be admixed so that the combined odors of the individual components produce a desired fragrance. Such perfume compositions are carefully balanced harmonious blends of essential oils, aroma chemicals, resinoids and other extracts of natural odorous materials. Each ingredient imparts its own characteristic effect in the composition. Thus, one or more of the norcamphanyl-substituted pyrans of this invention can be employed to impart novel characteristics into fragrance compositions.

Such compositions may contain up to about 80 weight percent of any one or more of the norcamphanyl-substituted pyrans of this invention. Ordinarily, at least about 0.001 weight percent of the norcamphanyl-substituted pyran is required to impart significant odor characteristics. Amounts in the range of from about 1 to about 60 weight percent are preferred. The norcamphanyl-substituted pyrans of this invention may be formulated into concentrates containing from about 1 to about 60 weight percent of the chemical in an appropriate solvent. Such concentrates are then employed to formulate products such as colognes, soaps, etc., wherein the concentration of the chemical of this invention can be in the range of from about 0.001 to about 7 weight percent, depending upon the final product. For example, the concentration of the chemical of this invention will be of the order of about 0.001 to about 0.1 percent in detergents, and of the order of about 0.01 to about 7 weight percent in perfumes and colognes.

The norcamphanyl-substituted pyrans of this invention are useful as olfactory components of perfume compositions for detergents and soaps; space odorants and deodorants; perfumes; colognes; toilet water; bath preparations such as bath oils and bath solids; hair preparations such as lacquers, brilliantines, pomades and shampoos; cosmetic preparations such as creams, deodorants, hand lotions and sunscreens; powders such as talcs, dusting powders and face powders; and the like.

The following Examples are illustrative of the present invention.

EXAMPLE 1

Concentrated (97%) sulfuric acid (0.3 g) was added to 2-methyl-1-penten-4-ol (374 g) with stirring under nitrogen at 69° C., and stirring was continued for 0.4 hour at 68°–71° C. Camphene epoxide (446 g) dissolved in hexane (450 ml) was added to the mixture during one hour at 53°±2° C. Heating was not required for the first half of this mildly exothermic reaction. A Dean-and-Stark trap was introduced, and the reaction mixture was heated at 87°–89° C. and vigorously agitated for 4 hours, during which time 38.5 ml of water was collected.

The reaction mixture was washed with 2% sodium bicarbonate solution (100 ml) and water (300 ml). Volatiles were distilled through a 6"×1⅜" I.D. column packed with large Raschig rings (steam bath, water-ejector vacuum). The pot temperature did not exceed 95° at 140 mm Hg. The crude product (761 g) remaining in the pot was fractionated through the same column, and after a fore-run, a fraction (321 g), b$_2$ 107°–112° was collected.

Figure 2:
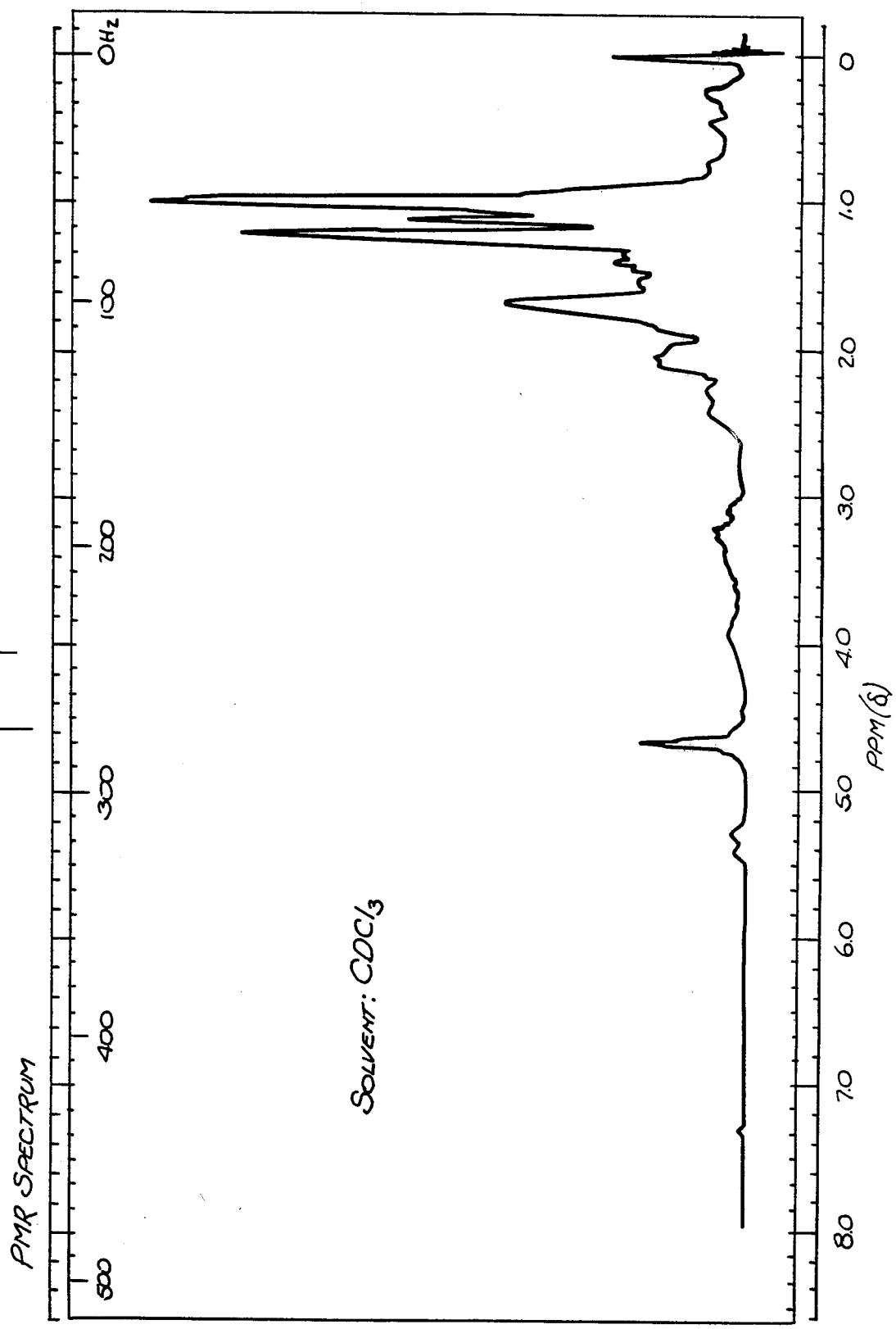
FIG. 2 is the proton magnetic resonance spectrum of the product of Example 1.
Figure 3:
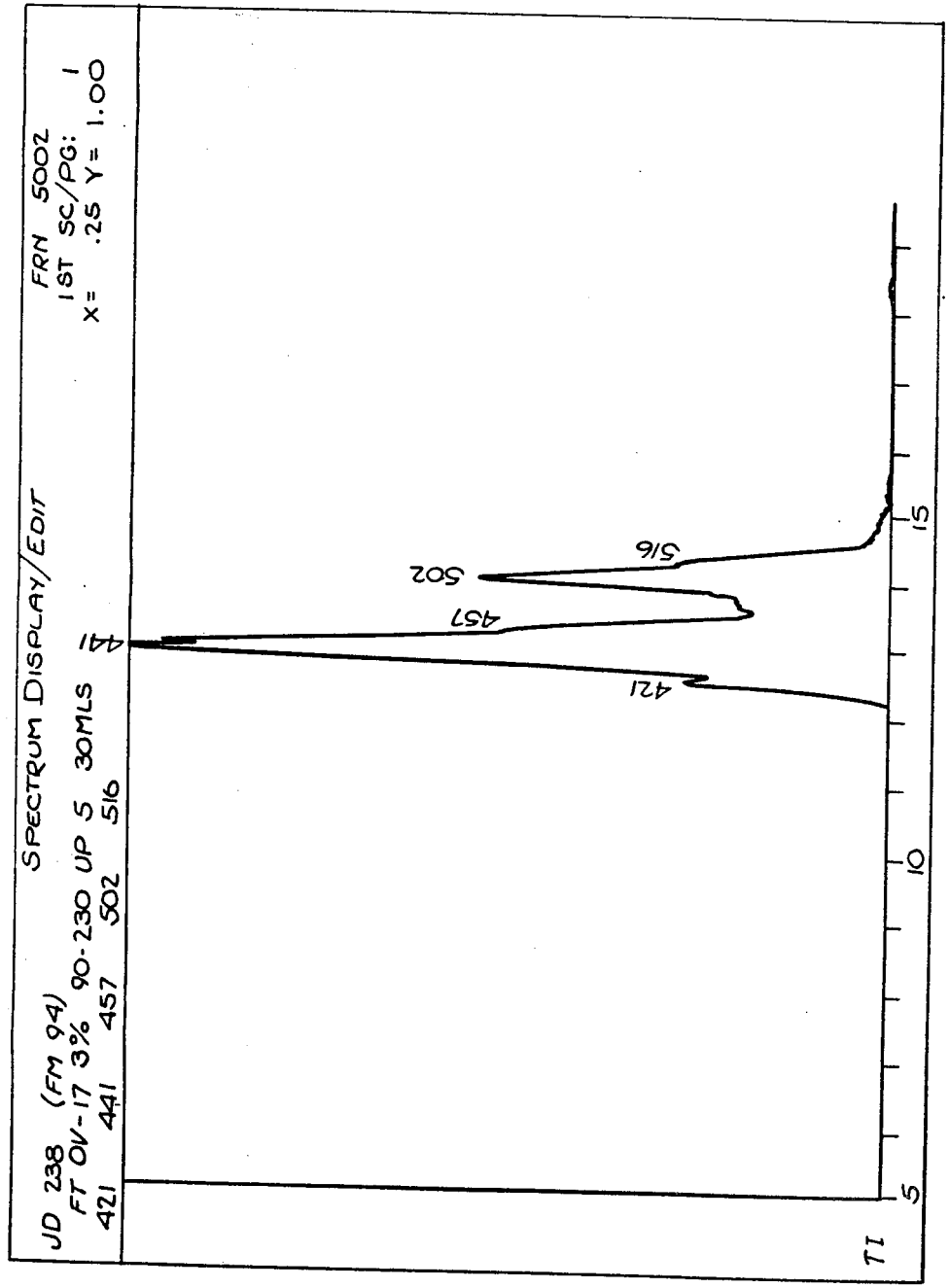
FIGS. 3 and 4 represent the mass spectral data of the product of Example 1.
Figure 4:
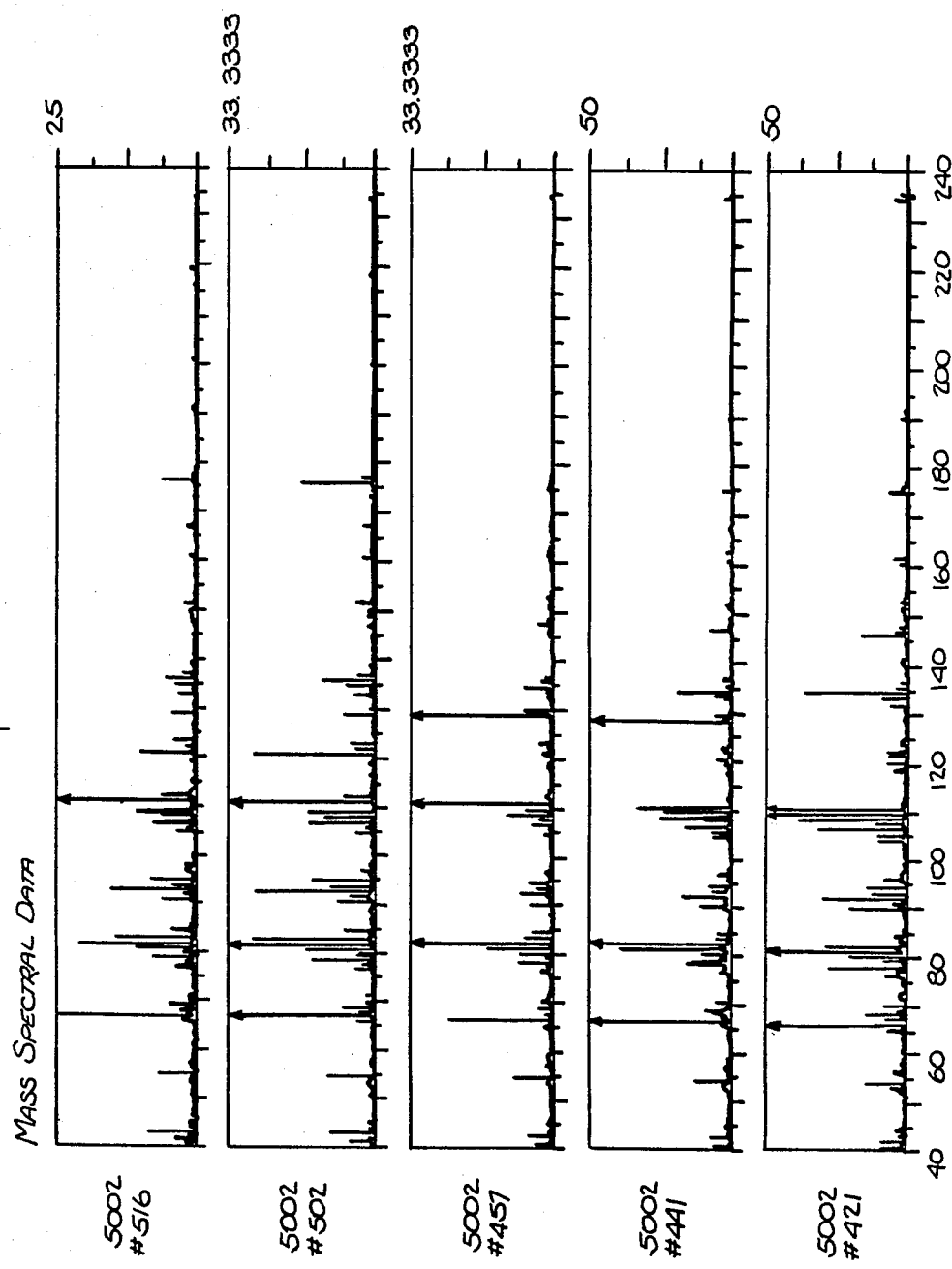

The product is a mixture of chemicals having the structures:

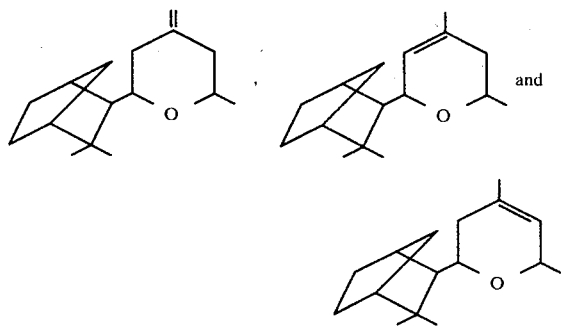

as confirmed by the infra-red, pmr and mass spectral data shown in FIGS. 1–4. This product has a soft, dry woody odor with greenpepper notes. If desired the isomers can be separated by preparative chromatography techniques known to the art. However, such separation is not necessary, and the mixture of isomers can be employed as is. Employing similar procedures, except that 2,2-dimethylbicyclo[2.2.1]heptane-3-carboxaldehyde was substituted for camphene epoxide, a mixture of the same chemicals has been obtained.

EXAMPLE 2

Employing procedures and materials similar to those described in Example 1, except that 2-methyl-1-buten-4-ol is substituted for 2-methyl-1-penten-4-ol, there can be produced a mixture of chemicals having the structures:

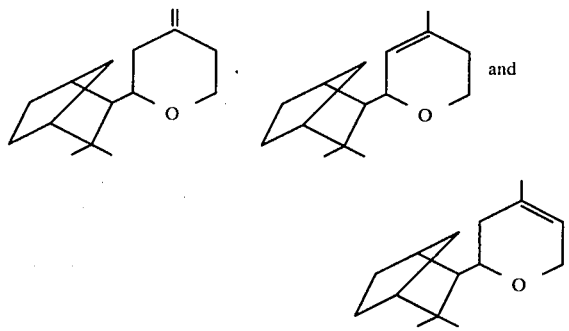

EXAMPLE 3

LAVENOL PERFUME FORMULATION

The norcamphanyl-substituted pyran mixture prepared according to Example 1 is incorporated in the lavender type perfume formulation specified below to impart its characteristic odor.

| Ingredient | Parts by Weight |
| --- | --- |
| OIL ESTRAGON EXTRA | 1.5 |
| OIL PETITGRAIN PARAGUAY | 1.8 |
| MUSK T SPECIAL | 3.0 |
| OIL LIME DISTILLED | 3.0 |
| HYPERESSENCE LIATRIX INCOLORE | 3.0 |
| OIL CLOVE EXTRA | 3.0 |
| OIL CANANGA | 3.5 |
| OIL PETITGRAIN CITRONNIER | 3.7 |
| OIL ROSEMARY EXTRA | 3.8 |
| OIL NEROLI | 8.2 |
| OIL MANDARIN EXPRESSED | 8.3 |
| OIL PATCHOULY | 10.0 |
| GERANYL ACETATE | 10.0 |
| TERPINYL ACETATE | 11.0 |
| MUSK AMBRETTE | 11.3 |
| LINALYL ACETATE SYNTHETIC | 20.0 |
| OIL SPIKE LAVENDER EXTRA | 20.0 |
| SANDELA GD | 20.0 |
| VANILLIN | 85.1 |
| TINCTURE AMBERGRIS 4:128 | 24.0 |
| LINALOOL SYNTHETIC | 24.0 |
| OIL SAGE CLARY | 30.0 |
| OIL ORANGE BITTER WEST INDIAN | 30.5 |
| OIL AMYRIS | 35.0 |
| OIL GERANIUM ALGERIAN EXTRA | 40.0 |
| OIL LIME EXPRESSED | 44.0 |
| HELIOTROPIN EXTRA | 50.0 |
| OIL LEMON COLD PRESSED | 63.5 |
| COUMARIN | 103.7 |
| OIL LAVENDER FCC BARREME 38–42% | 97.8 |
| OIL LAVANDIN ABRIAL EXTRA | 152.0 |
| THE NORCAMPHANYL-SUBSTITUTED PYRAN PRODUCT OF EXAMPLE 1 | 225.3 |
| TOTAL | 1150.0 |

EXAMPLE 4

AMBRE PERFUME FORMULATION

The norcamphanyl-substituted pyran product of Example 1 is incorporated in the following Labdanum type perfume formulation to impart its characteristic odor.

| Ingredient | Parts by Weight |
| --- | --- |
| CASTOREUM ABSOLUTE | 1 |
| VANILLIN | 2 |
| RESINOID OLIBANUM EXTRA | 2 |
| 10% SOL. OIL BALSAM PERU IN D.E.P. | 2 |
| 50% SOL. RESINOID BENZOIN SIAM EXTRA IN D.E.P. | 4 |
| RESINOID TOLU | 8 |
| RESINOID ABSOLUTE LABDANUM FB | 25 |
| THE NORCAMPHANYL-SUBSTITUTED PYRAN PRODUCT OF EXAMPLE 1 | 56 |
| TOTAL | 100 |

EXAMPLE 5

AMBREINE PERFUME FORMULATION

The norcamphanyl-substituted pyran product of Example 1 is incorporated in the perfume composition specified below.

| Ingredient | Parts by Weight |
| --- | --- |
| METHYL NAPHTHYL KETONE | 0.2 |
| NOVOVIOL ALPHA | 0.2 |
| ALDEHYDE C-14 | 0.2 |
| 10% SOL. BENZALDEHYDE IN D.E.P. | 0.4 |
| OIL NEROLI | 0.5 |
| 3% SOL. MUSQUIN IN ALCOHOL | 1.0 |
| 10% SOL. ABSOLUTE IMMORTELLE IN D.E.P. | 1.0 |
| 50% SOL. CASTOREUM ABSOLUTE IN D.E.P. | 1.0 |
| PHENYL ETHYL ALCOHOL | 1.0 |
| 10% SOL. OIL OLIBANUM EXTRA IN D.E.P. | 1.0 |
| OIL ORANGE SWEET WEST INDIAN | 1.0 |
| METHYL IONONE GAMMA PURE | 1.5 |
| OIL PATCHOULY LIGHT COLOR | 2.0 |
| 50% SOL. OILBANUM EXTRA RESINOID IN D.E.P. | 2.0 |
| 10% SOL. OIL GALBANUM IN D.E.P. | 2.0 |
| 50% SOL. CYSTE ABSOLUTE IN D.E.P. | 3.0 |
| ETHYL VANILLIN | 3.0 |
| MUSK XYLOL | 3.0 |
| STYRAX RESINOID | 4.0 |
| OIL CEDARWOOD WHITE TEXAS | 6.0 |
| VANILLIN | 7.5 |
| OIL LEMON COLD PRESSED | 8.0 |
| 50% SOL. Benzoin SIAM RESINOID EXTRA IN D.E.P. | 11.0 |
| COUMARIN | 15.5 |
| OIL BERGAMOT SYNTHETIC | 24.0 |
| THE NORCAMPHANYL-SUBSTITUTED PYRAN PRODUCT OF EXAMPLE 1 | 25.0 |
| TOTAL | 125.0 |

This invention has been described in terms of specific embodiments set forth in detail, but it should be understood that these are by way of illustration only and that the invention is not necessarily limited thereto. Other modifications and variations will be apparent from this disclosure and may be resorted to without departing from the spirit of this invention, as those skilled in the art will readily understand. Accordingly, such variations and modifications are considered to be within the scope of this invention and the following claims.

What is claimed is:

1. A perfume composition comprising from about 0.001 to about 80 weight percent of a norcamphanyl-substituted pyran of the formula:

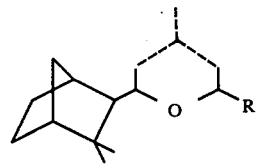

wherein the dashed lines represent either a carbon-carbon single bond or a carbon-carbon double bond such that two of the three dashed lines represent carbon-carbon single bonds; and wherein R is either hydrogen or a methyl group in admixture with at least one perfume ingredient.

2. A composition according to claim 1 containing from about 1 to about 60 weight percent of said norcamphanyl-substituted pyran.

3. A composition according to claim 1 containing from about 0.001 to about 7 weight percent of said norcamphanyl-substituted pyran.

* * * * *

UNITED STATES PATENT AND TRADEMARK OFFICE
CERTIFICATE OF CORRECTION

PATENT NO. : 4,271,046
DATED : June 2, 1981
INVENTOR(S) : Brian J. Willis and John W. Dittrick It is certified that error appears in the above—identified patent and that said Letters Patent is hereby corrected as shown below:

Column 2, lines 50-51, should read -- wherein the dashed lines represent either a carbon-carbon single bond or a carbon-carbon double bond; and wherein the presence of three dashed lines --.

Signed and Sealed this

Fifteenth Day of December 1981

[SEAL]

Attest:

GERALD J. MOSSINGHOFF

Attesting Officer     Commissioner of Patents and Trademarks